United States Patent [19]

Powell

[11] Patent Number: 4,692,200
[45] Date of Patent: Sep. 8, 1987

[54] SELF-VENTING BALLOON DILATATION CATHETER AND METHOD

[75] Inventor: Philip E. Powell, Mountain View, Calif.

[73] Assignee: Advanced Cardiovascular Systems, Inc., Mountain View, Calif.

[21] Appl. No.: 907,108

[22] Filed: Sep. 15, 1986

Related U.S. Application Data

[62] Division of Ser. No. 760,637, Jul. 30, 1985, Pat. No. 4,638,805.

[51] Int. Cl.[4] .............................................. B29C 27/00
[52] U.S. Cl. ................................... 156/289; 156/294; 128/344
[58] Field of Search ................ 156/289, 294; 128/344; 604/96, 103

[56] References Cited

U.S. PATENT DOCUMENTS

| | | | |
|---|---|---|---|
| 4,154,244 | 5/1979 | Becker et al. | 156/294 X |
| 4,251,305 | 2/1981 | Becker et al. | 156/289 X |
| 4,263,236 | 4/1981 | Briggs et al. | 156/294 X |
| 4,284,459 | 8/1981 | Patel et al. | 156/294 X |
| 4,490,420 | 12/1984 | Yoshida | 156/289 X |
| 4,622,091 | 11/1986 | Letterman | 156/289 X |

Primary Examiner—Carlton R. Croyle
Assistant Examiner—Theodore Olds
Attorney, Agent, or Firm—Flehr, Hohbach, Test, Albritton & Herbert

[57] ABSTRACT

Self-venting balloon dilatation catheter having a flexible tubular member with first and second lumens extending therethrough. An inflatable balloon is carried by the distal extremity of the tubular member in such a manner so that the first lumen extends through the balloon and is out of communication with the interior of the balloon and the second lumen is in communication with the interior of the balloon. A venting device is disposed between the balloon and the tubular member for venting air from the interior of the balloon but inhibiting the escape of liquid from the balloon.

3 Claims, 4 Drawing Figures

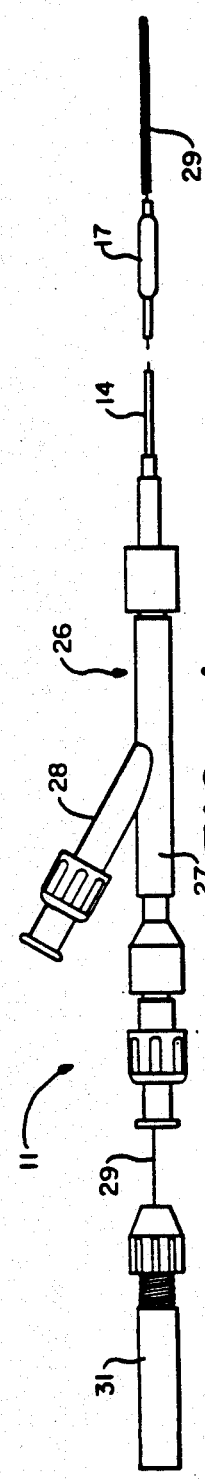
FIG.—1
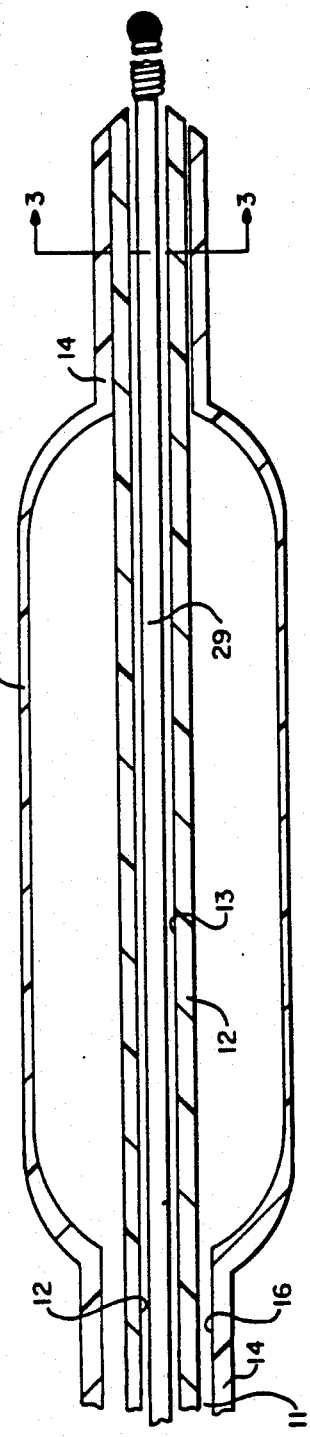
FIG.—2
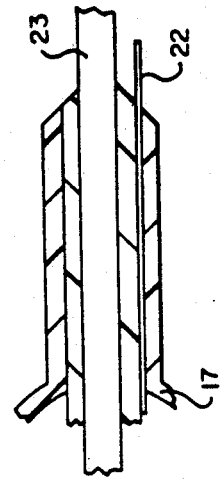
FIG.—4
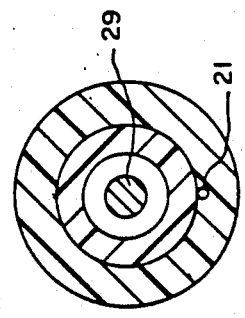
FIG.—3

SELF-VENTING BALLOON DILATATION CATHETER AND METHOD

This is a division of application Ser. No. 760,637, filed July 30, 1985, now U.S. Pat. No. 4,638,805.

This invention relates to balloon dilatation catheters and more particularly to such catheters having a self-venting balloon and a method for making the same.

In utilizing balloon dilatation catheters, it is necessary that the balloon be filled with a liquid. In the filling of the balloon, it is desirable that the air which is within the balloon be expelled from the balloon but the air is compressible. In the past this has been accomplished by successively aspirating the balloon with fluid. The air is withdrawn during the repeated evacuation. This has a disadvantage in that it can be difficult to ensure complete removal of all the air. Alternatively, the air removal is accomplished by providing a separate tube which may be removable which extends from the proximal extremity of the catheter into the balloon so that during the time that the liquid is being introduced into the ballon, the air in the balloon can be expelled through the separate tube. The use of such a separate tube has a disadvantage, particularly when it is desired to provide a dilatation catheter which has a very low profile in that it makes it more difficult to reduce the profile of the dilatation catheter. There is therefore a need for a new and improved balloon dilatation catheter which overcomes these limitations.

In general, it is an object of the present invention to provide a balloon dilatation catheter which is self-venting.

Another object of the invention is to provide a dilatation catheter of the above character in which the air is vented through the distal extremity of the catheter.

Another object of the invention is to provide a balloon dilatation catheter of the above character in which the air in the balloon is vented while the leakage of any liquid from the balloon is inhibited.

Another object of the invention is to provide a balloon dilatation catheter of the above character which ensures complete removal of the air without aspiration.

Another object of the invention is to provide a method for constructing the catheter of the present invention.

Additional objects and features of the invention will appear from the following description in which the preferred embodiment is set forth in detail in conjunction with the accompanying drawing.

FIG. 1 is a side elevational view of a balloon dilatation catheter incorporating the present invention.

FIG. 2 is a cross sectional view of the distal extremity of the balloon dilatation catheter shown in FIG. 1.

FIG. 3 is a cross sectional view taken along the line 3—3 of FIG. 2.

FIG. 4 is a cross sectional view showing the method which is utilized in manufacturing the balloon dilatation catheter shown in FIGS. 1–3.

In general, the self-venting balloon dilatation catheter of the present invention is comprised of a flexible tubular member having first and second lumens extending therethrough. An inflatable balloon is carried by the distal extremity of the tubular member in such a manner so that the first lumen extends through the balloon and is out of communication with the interior of the balloon and the second lumen is in communication with the interior of the balloon. A vent system is disposed between the balloon and the tubular member for venting air from the interior of the balloon but inhibiting the escape of liquid from the balloon.

More in particular as shown in FIGS. 1–3 of the drawing, the balloon dilatation catheter 10 incorporating the present invention is comprised of a tubular member 11 which consists of a first tubular element 12 which has a lumen 13 extending therethrough. It also consists of a second tubular element 14 which is coaxially disposed on the first tubular element 12 and provides in conjunction with the first tubular element an annular lumen which extends longitudinally of the first and second tubular elements 12 and 14. An expandable balloon 17 is carried by the second tubular element 14 of the member 11 near the distal portion thereof and has its interior in communication with the lumen 16. The balloon 17 extends concentrically about the first tubular element 12. Although the balloon 17 can be formed as a separate element which has its extremities bonded to the second tubular element 14, it is preferably formed integral with the second tubular element as shown. The tubular elements 12 and 14 are formed of a suitable flexible thermo-plastic material such as a polyolefin or polyvinylchloride.

The distal extremities of the first and second tubular elements 12 and 14 are bonded together in a suitable manner so as to form a liquid-tight seal between the same. Typically this can be accomplished by applying heat to the distal extremity of the second tubular element with a mandrel disposed in the distal extremity of the first tubular element and applying heat to shrink the distal extremity of the second tubular element onto the first tubular element to form such a seal.

Means is provided in the distal extremity of the first and second tubular elements for venting air from the balloon 17 while inhibiting the escape of liquid from the balloon 17 and consists of a very small passage 21 which is disposed between the distal extremities of the first and second tubular elements 12 and 14 and which extends from the interior of the balloon 17 to ambient at the distal extremity of the catheter 11. The flow passage 21 can be formed in any suitable manner. One method found to be particularly efficacious is as follows in conjunction with FIG. 4. A piece 22 of suitable wire such as tungsten is used because of its good tensile strength. The wire 22 should have a diameter which is less than 0.001 inches as, for example, 0.0005 inches. It is coated with silicone. After the wire 22 has been coated with silicone, it is inserted by a tweezers between the distal extremities of the first and second tubular elements 12 and 14 prior to the time that the second tubular element 14 is heat shrunk onto the first tubular element as hereinbefore described. As soon as the tungsten wire 22 has been inserted into the distal extremities of the first and second tubular elements 12 and 14 so that it extends into the balloon 17 and out the distal extremities as shown in FIG. 4, a mandrel 23 is inserted into the lumen 13. Heat is then applied to the distal extremity of the second tubular element 14 to cause it to form a shrink fit between it and the distal extremity of the first tubular element 12 and at the same time to shrink down around the wire 22. After the distal extremity of the catheter has been cooled, the mandrel 23 can be removed and the wire 22 can be pulled out with tweezers leaving the cylindrical flow passage 21 hereinbefore described.

It should be appreciated that if desired, more than one hole or passage 21 can be provided to make the balloon venting procedure more rapid. It also should be appreciated that other means can be provided in the distal extremity of the catheter in place of the passage 21 for making the balloon 17 self-venting. For example, braided fibers can be utilized in the distal extremity of the catheter in the same manner as the tungsten wire 22 has been utilized. In such a case, the fibers can be left in place so that the air can flow between interstices of the braided fibers. Alternatively, hollow fiber or fibers can be incorporated into the distal extremity of the catheter. Alternatively, hydrophobic filter material can be incorporated between the distal extremities of the first and second tubular elements 12 and 14. This filter material is capable of passing air but inhibits the passage of liquid from the balloon 17.

The remainder of the balloon dilatation catheter shown in FIG. 1 is substantially conventional. A side arm adapter 26 is provided which has a main or central arm 27 and a side arm 28. A guide wire 29 extends through the main or central arm 27 and extends through the lumen 13 of the first tubular element 12 and has a distal extremity extending beyond the distal extremity of the dilatation catheter 11. A torquer 31 is secured to the proximal extremity of the guide wire 29 and is utilized for extending and retracting the guide wire and also for rotating the guide wire.

Use of the self-venting balloon dilatation catheter may now be briefly described as follows. The balloon 17 is first inflated outside of the human body by introducing a radiographic contrast liquid through the side arm 28 so that is passes through the annular lumen 16 between the first and second tubular elements 12 and 14 and passes into the balloon 17. The air which is in the balloon is pushed forwardly in the balloon and under the pressure of the radiographic contrast liquid is forced to pass out through the small passage 21 provided between the distal extremities of the first and second tubular elements 12 and 14. By utilizing a passage 21 having a diameter of 0.0005 inches, it has been found that a two millimeter diameter balloon having a length of approximately 25 millimeters can be completely rid of air in less than approximately 40 seconds. The size of the passage 21 is such that it inhibits the escape of the radiographic contrast liquid so that very little, if any, of the liquid can escape, even though pressures up to 200 psi for the radiographic contrast liquid is attained within the balloon 17. As soon as the balloon 17 has been inflated with the radiographic contrast liquid and the air has been expelled therefrom through the passage 21, the liquid can be withdrawn to deflate the balloon 17. The balloon dilatation catheter is now ready to be inserted into the human body. After the balloon 17 has been positioned in the stenosis in the arterial vessel in the human body, the balloon can be again inflated by reintroducing radiographic contrast liquid through the side arm 28 through the lumen 16 and into the balloon 17. Since all of the air has previously been expelled from the balloon 17, the balloon can be readily inflated within the stenosis to its full diameter at the desired pressure as, for example, in excess of 100 psi without danger of any significant amount of radiopaque contrast liquid passing through the passage 21. After the opening in the stenosis has been enlarged, the balloon can be deflated and the dilatation catheter can be removed.

It is apparent from the foregoing that there has been provided a balloon dilatation catheter which is self-venting and in which the balloon can be inflated to the desired pressure without danger of any significant amount of radiopaque contrast liquid passing through the venting orifice provided in the distal extremity of the balloon dilatation catheter. The venting orifice formed in the distal extemity of the balloon dilatation catheter is formed in such a manner so that it can be readily incorporated into the manufacturing process for making the balloon dilatation catheters.

What is claimed is:

1. In a method for fabricating a self-venting balloon dilatation catheter, providing a first tubular element having a lumen extending therethrough, providing a second tubular element having a lumen disposed therein, forming a balloon onto the second tubular element near the distal extremity of the second tubular element, placing the first tubular element within the second tubular element so that the second tubular element extends coaxially of the first tubular element and forming a flow passage open to ambient between the distal extremities of the first and second tubular elements and in communication with the interior of the balloon which has a size less than 0.001 inches to permit the escape of air from the interior of the balloon but inhibiting the escape of liquid from the interior of the balloon.

2. In a method for fabricating a self-venting balloon dilatation catheter, providing a first tubular element having a lumen extending therethrough, providing a second tubular element having a lumen disposed therein, forming a balloon onto the second tubular element near the distal extremity of the second tubular element, placing the first tubular element within the second tubular element so that the second tubular element extends coaxially of the first tubular element, forming a flow passage between the distal extremities of the first and second tubular elements and in communication with the interior of the balloon which has a size less than 0.001 inches to permit the escape of air from the interior of the balloon but inhibiting the escape of liquid from the interior of the balloon, said flow passage being formed by introducing a wire between the distal extremities of the first and second tubular elements, forming the second tubular element of a heat shrinkable plastic, placing a mandrel in the lumen of the first tubular element in the distal extremity of the first tubular element, applying heat to the distal extremity of the second tubular element to heat shrink it onto the first tubular element, permitting the distal extremities of the first and second tubular elements to cool, removing the mandrel from the lumen of the first tubular element and removing the wire from between the first and second tubular elements to provide the flow passage.

3. A method as in claim 2 wherein said wire is formed of tungsten to facilitate the transfer of heat and to facilitate removal of the wire.

* * * * *